United States Patent
Zhou et al.

(10) Patent No.: US 9,492,645 B2
(45) Date of Patent: *Nov. 15, 2016

(54) SKIN TREATMENT DEVICE WITH AN INTEGRATED SPECIMEN DISPENSER

(75) Inventors: Yuchen Zhou, San Jose, CA (US); Hieu Tieu, San Jose, CA (US); Chao Uei Wahng, Fremont, CA (US)

(73) Assignee: La Pierres, Inc., Pleasanton, CA (US)

( * ) Notice: Subject to any disclaimer, the term of this patent is extended or adjusted under 35 U.S.C. 154(b) by 982 days.

This patent is subject to a terminal disclaimer.

(21) Appl. No.: 13/396,381

(22) Filed: Feb. 14, 2012

(65) Prior Publication Data

US 2012/0209151 A1    Aug. 16, 2012

Related U.S. Application Data

(63) Continuation of application No. 13/317,136, filed on Oct. 11, 2011.

(60) Provisional application No. 61/456,164, filed on Nov. 2, 2010, provisional application No. 61/464,520, filed on Mar. 3, 2011.

(51) Int. Cl.
| | |
|---|---|
| *A61M 37/00* | (2006.01) |
| *A61M 35/00* | (2006.01) |
| *A61H 23/02* | (2006.01) |
| *A61H 7/00* | (2006.01) |
| *A61H 23/00* | (2006.01) |
| *A61N 5/06* | (2006.01) |
| *A61N 1/32* | (2006.01) |

(52) U.S. Cl.
CPC ............ *A61M 35/003* (2013.01); *A61H 7/005* (2013.01); *A61H 23/006* (2013.01); *A61H 23/02* (2013.01); *A61H 23/0245* (2013.01); *A61N 1/325* (2013.01); *A61N 1/328* (2013.01); *A61N 5/0616* (2013.01); *A61H 2201/10* (2013.01); *A61H 2201/105* (2013.01); *A61H 2201/1215* (2013.01); *A61H 2201/5005* (2013.01); *A61H 2201/5035* (2013.01); *A61M 37/0092* (2013.01); *A61N 1/322* (2013.01); *A61N 2005/0644* (2013.01)

(58) Field of Classification Search
CPC .................. A61H 2201/10; A61H 2201/105; A61H 2201/1215; A61H 2201/5005; A61H 2201/5035; A61H 23/00; A61H 23/02; A61H 23/006; A61H 23/0245; A61H 7/005; A61N 1/325; A61N 1/328; A61N 1/322; A61N 5/0616; A61N 2005/0644; A61M 37/0092; A61M 35/003
USPC ...... 601/2, 3, 15, 17, 18, 46, 47, 48, 53, 57, 601/78, 80, 81, 84, 89, 92, 93, 97, 101, 103, 601/107, 108, 111, 134, 135, 136, 137; 604/22
See application file for complete search history.

(56) References Cited

U.S. PATENT DOCUMENTS

| | | | |
|---|---|---|---|
| 8,523,791 B2 * | 9/2013 | Castel | ............................ 601/15 |
| 2007/0185553 A1 * | 8/2007 | Kennedy | .............. A61N 5/0616 607/100 |

(Continued)

*Primary Examiner* — Quang D Thanh
(74) *Attorney, Agent, or Firm* — Dahyee Law Group; Leon E. Jew; Rouzbeh Alani

(57) ABSTRACT

An electronic skin treatment device with an integrated specimen dispenser is disclosed, with which specimen dispense can be concurrently applied to target skin area while ultrasonic vibrations, mechanical massaging motions, galvanic stimulations, or light illuminations are used and as such a customizable, easier and better skin beautification can be achieved.

9 Claims, 11 Drawing Sheets

(56) References Cited

U.S. PATENT DOCUMENTS

| | | | |
|---|---|---|---|
| 2008/0139974 A1* | 6/2008 | Da Silva | 601/2 |
| 2012/0089081 A1* | 4/2012 | Chao Uei et al. | 604/22 |
| 2012/0109043 A1* | 5/2012 | Zhou et al. | 604/20 |
| 2012/0245730 A1* | 9/2012 | Zhou et al. | 700/231 |

* cited by examiner

SKIN TREATMENT DEVICE WITH AN INTEGRATED SPECIMEN DISPENSER

CROSS REFERENCE TO RELATED APPLICATIONS

This application is a continuation-in-part of and claims the benefit of priority to U.S. patent application Ser. No. 13/317,136, entitled "Integrated skin-treatment specimen dispenser with electrical interface," filed on Oct. 11, 2011, which claims the benefit of domestic priority to U.S. provisional application Ser. No. 61/456,164 filed on Nov. 2, 2010, entitled "Integrated skin-treatment specimen dispenser with electrical interface," the content of which being incorporated in its entirety by reference herein.

This application is based on, and claims the benefit of priority to, U.S. provisional application Ser. No. 61/464,520, entitled "Skin treatment device with an integrated specimen dispenser," filed on Mar. 3, 2011, the content of which being incorporated in its entirety by reference herein. If any part of this application is not qualified to claim the benefit of priority to U.S. patent application Ser. No. 13/317,136 with a domestic priority of Nov. 2, 2010, then the nonqualified part claims the benefit of priority to U.S. provisional application Ser. No. 61/464,520 filed on Mar. 3, 2011.

The application is also related to (1) U.S. patent application Ser. No. 12/925,017, entitled "Ultrasonic device with integrated specimen dispenser," filed on Oct. 12, 2010, (2) U.S. patent application Ser. No. 12/932,316, entitled "Massaging device with multiple ultrasonic transducers," filed on Feb. 22, 2011, which claims the benefit of priority to U.S. provisional application Ser. No. 61/404,923 filed on Oct. 12, 2010, and (3) U.S. patent application Ser. No. 13/317,203, entitled "Piezoelectric element driver", filed on Oct. 11, 2011, which claims the benefit of priority to U.S. provisional application Ser. No. 61/404,922 filed on Oct. 12, 2010 and to U.S. provisional application Ser. No. 61/456,164 filed on Oct. 2, 2010, the contents of which are incorporated in their entirety by reference herein.

FIELD OF THE INVENTION

The present invention generally relates to electrical and electronic massage technology and more particularly to a skin treatment device with an integrated specimen dispenser.

BACKGROUND OF THE INVENTION

Skin treatment with electronic devices is a widely accepted method to enhance skin beautification process to achieve better results than application of cream, lotion and serum products alone. The devices usually introduce certain kind of physical means to the human skin to either help activate chemical molecules within the cream or lotion or serum products, or help such molecules further penetrate into the skin by agitating the skin cells and opening up chemical pathways into the cells.

The inventors believe that the following listed are relevant prior arts: (1) Y. Mitsu, "Skin beautification cosmetic system using iontophoresis device, ultrasonic facial stimulator, and cosmetic additive," U.S. Pat. No. 7,427,273 B2 (2008); (2) M. Nunomura, and T. Oba, "ultrasound applying skin care device," Pub. No. US 2006/0149169 (2006); (3) U. Motoyoshi, "ULTRASONIC FACIAL AND BEAUTY APPLIANCE," Pub. No. JP2007050204 (A) (2007); (4) H. Hisao, "ULTRASONIC FACE MASSAGER," Pub. No. JP2001314473 (A) (2001); (5) J. Reed, and et al, "Ultrasound based cosmetic therapy method and apparatus," Pub. No. US 2009/0318853 (2009); (6) D. G. Kern, "Galvanic current skin treatment," Pub. No. US 2007/0185431 A1 (2007); and (7) Z. Geva, and et al, "Multi-application skin care system," Pub. No. US 2011/0106067 A1 (2011).

The physical means that are introduced to act on the skin may include ultrasound, powered brushing, powered vibration, powered tapping, electric current and light illumination. These electrically powered physical means increase the efficiency of skin treatment process.

However, in prior art devices, lotion, cream and serum products (referred to as "lotion" herein after) are either applied externally to the target skin area or directly onto the skin treatment surface, of the electronic device before treating the skin. In other prior arts, the lotion is also applied by an externally attached dispenser that itself is also the skin treatment element which requires being attached to main device before treatment and disposed after each treatment. In all these prior arts, the lotion is either applied from a lotion container that is separated from the electronic device or externally attached to the electronic device, which all require operation by both hands of the user to apply the lotion or install container before treatment. This process makes skin treatment by the prior art devices not suitable for on-the-go usage where single-hand operation is generally required.

Additionally, all prior art devices only uses skin care specimen of a pre-determined composition and does not allow for adjustment of the composition according to each different user's own skin condition.

Prior arts do not contain an integrated specimen dispenser that is functionally part of the device itself which requires no preparation before treatment process, and lacking of which limits the portability of prior art devices and ability of using the devices for anytime and anywhere purpose.

What is desired is an integrated specimen dispenser for the electronic massage devices.

SUMMARY OF THE INVENTION

By introducing an integrated specimen dispenser, the various types of electronic skin treatment devices can have much better portability, flexibility and feasibility of customized skin treatment. This integrated specimen dispenser may also be used to synthesize customized skin care specimen according to the different user's own skin condition.

In various embodiments of this invention, we described skin-treatment specimen dispenser being integrated within various electronic skin treatment devices.

It is an object of this invention to integrate a skin treatment specimen dispenser with a skin treatment electronic device to provide an ultra portable and hygiene solution to enable anytime and anywhere skin treatment.

It is yet another object of this invention to use a specimen dispenser with an electrical interface to further enhance portability, flexibility and customizability of skin treatment devices, and to personalize both the skin treatment process as well as the skin care specimen preparation before treatment process.

DETAILED DESCRIPTION OF THE INVENTION

Figure 1A:
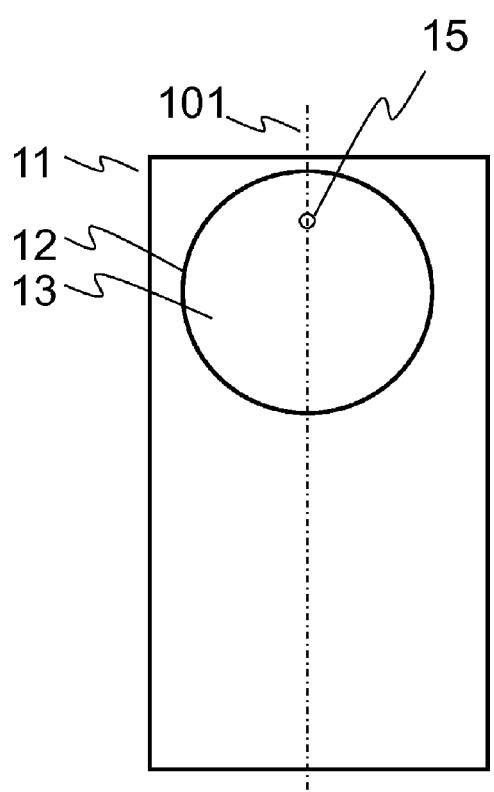
FIG. 1A is a schematic diagram illustrating the front view of the device according to the first preferred embodiment of the present invention.

While the present invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

First Embodiment

Figure 1B:
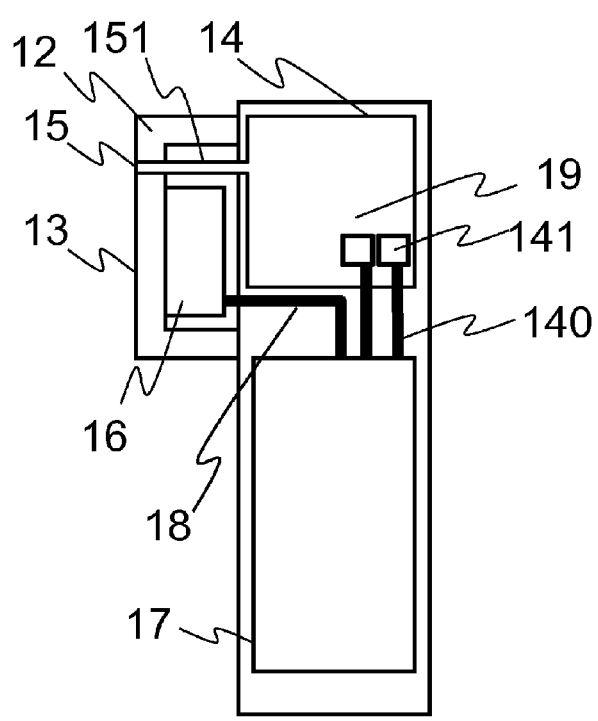
FIG. 1B is a schematic diagram illustrating a cross-sectional view of the device according to first preferred embodiment of the present invention.
Figure 1C:
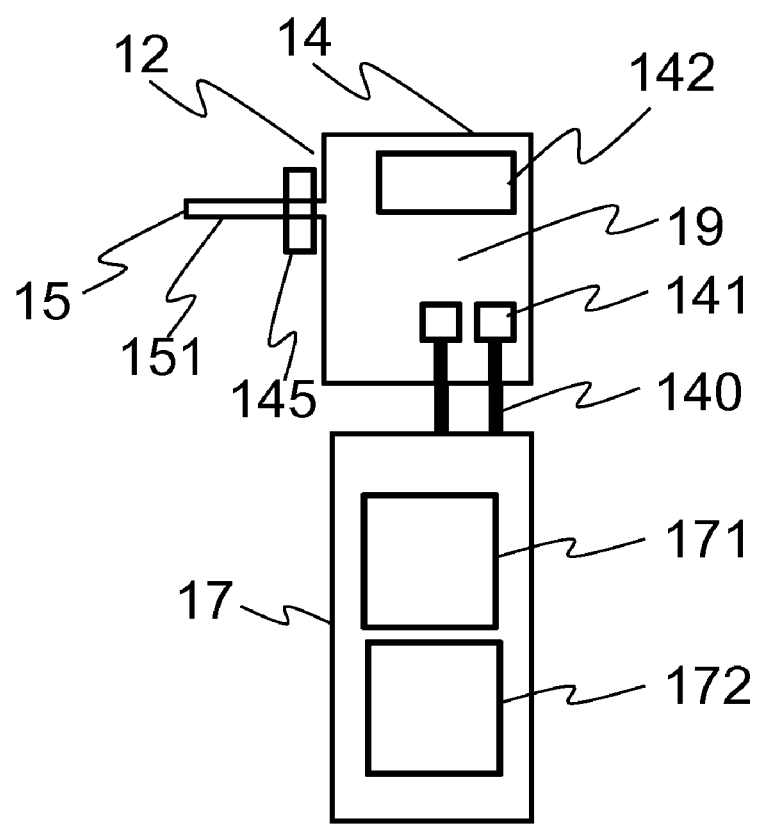
FIG. 1C is a schematic diagram illustrating components of the dispenser and the electronic control unit of the device according to the first preferred embodiment of the present invention.
Figure 1D:
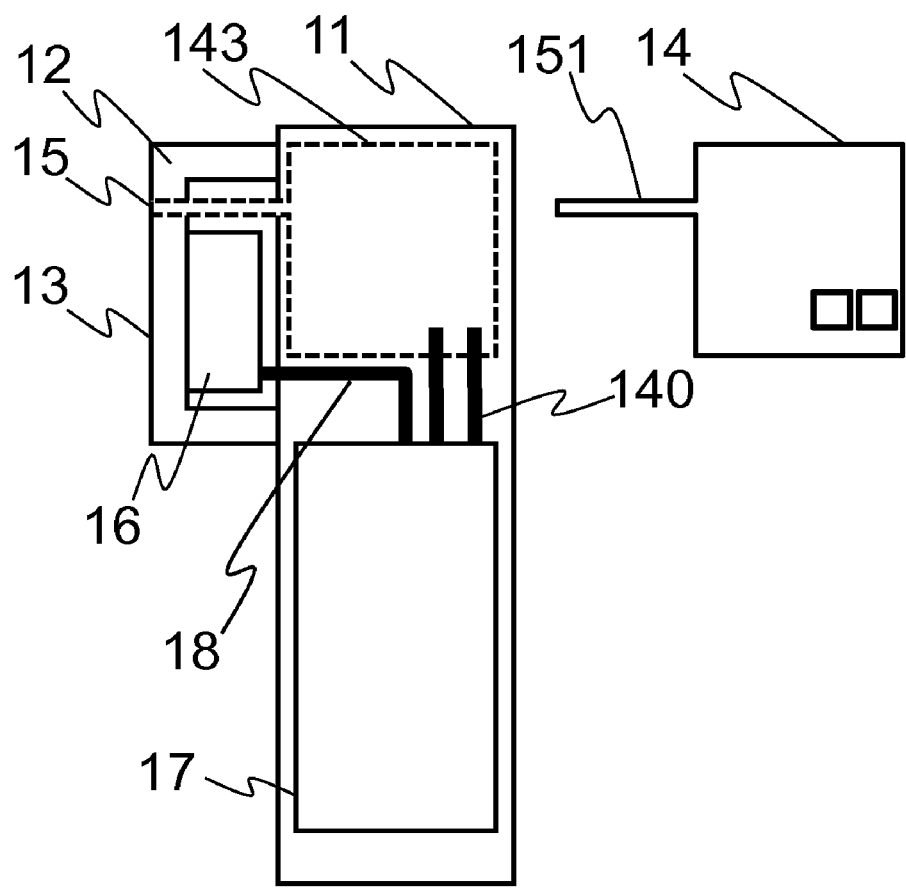
FIG. 1D is a schematic diagram illustrating the dispenser being removable from the device according to the first preferred embodiment of the present invention.
Figure 1E:
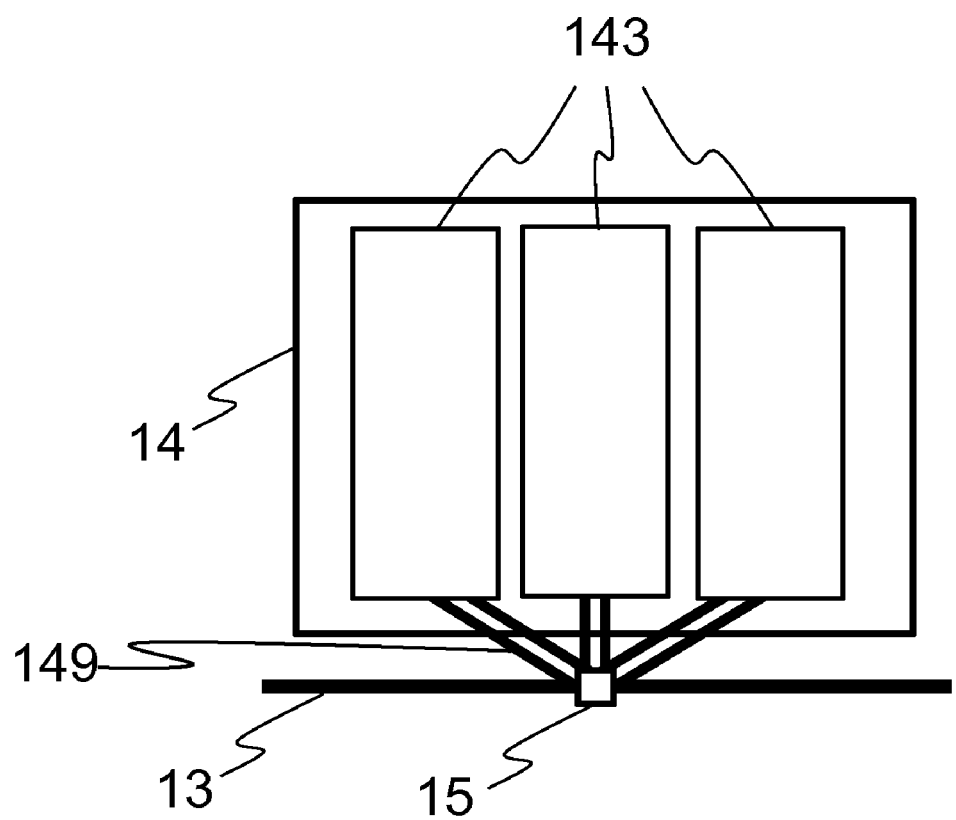
FIG. 1E is a schematic diagram illustrating an example of a specimen dispenser containing multiple sub-dispensers or multiple specimen compartments according to the first preferred embodiment of the present invention.

FIG. 1A through FIG. 1E illustrates the first preferred embodiment of the current invention, where a specimen dispenser is integrated within an ultrasound skin treatment device. FIG. 1A shows the front view of the proposed device. FIG. 1B shows the cross-section view along the center line 101 of FIG. 1A. FIG. 1C shows the cross-section view along the center line 101 of FIG. 1A with illustrating the components of the dispenser 14 and electronic control unit 17 of FIG. 1A. FIG. 1D illustrates the dispenser 14 being removable from the device enclosure body 11. FIG. 1E shows an example of specimen dispenser containing multiple sub-dispensers or multiple specimen compartments.

The first embodiment, which represents the best mode of this invention, contains the following aspects: (1) an enclosure body 11 which is made of metal, alloy or plastics; (2) an ultrasound transmission plate 12 for contacting the skin with a smooth treatment surface 13 and transmitting ultrasonic vibration generated by an ultrasound generator 16 to the target skin area; (3) a skin treatment specimen container and a dispenser, collectively referred to as dispenser 14 that contains skin treatment specimen 19 which can be, but not limited to, liquid, gel, cream, paste and powder; (4) a specimen outlet 15 existing on the same continuous surface 13 of the ultrasound transmission plate 12, through which skin treatment specimen 19 is dispensed close to or, preferably, directly on top of the surface 13 that is to be in contact with the skin during skin treatment; (5) an electronic control unit 17 containing electrical circuits, and electronic components 171 and necessary embedded software exists within the enclosure body 11; and (6) an electrical interface 18 exists between the ultrasound generator 16 and the electronic control unit 17 so that the performance of the ultrasound generator 16 can be controlled by the electronic control unit 17. The electronic control unit 17 controls ultrasonic generation from 16, and may also provide user interface, power supply and charging functions. Additionally, the electronic control unit 17 may send electrical signals to the specimen dispenser 14 or receives electrical signals from the specimen dispenser 14 to achieve required skin treatment procedure through another electrical interface 140 that connects to the electrical contacts 141 on dispenser 14.

Figure 6A:
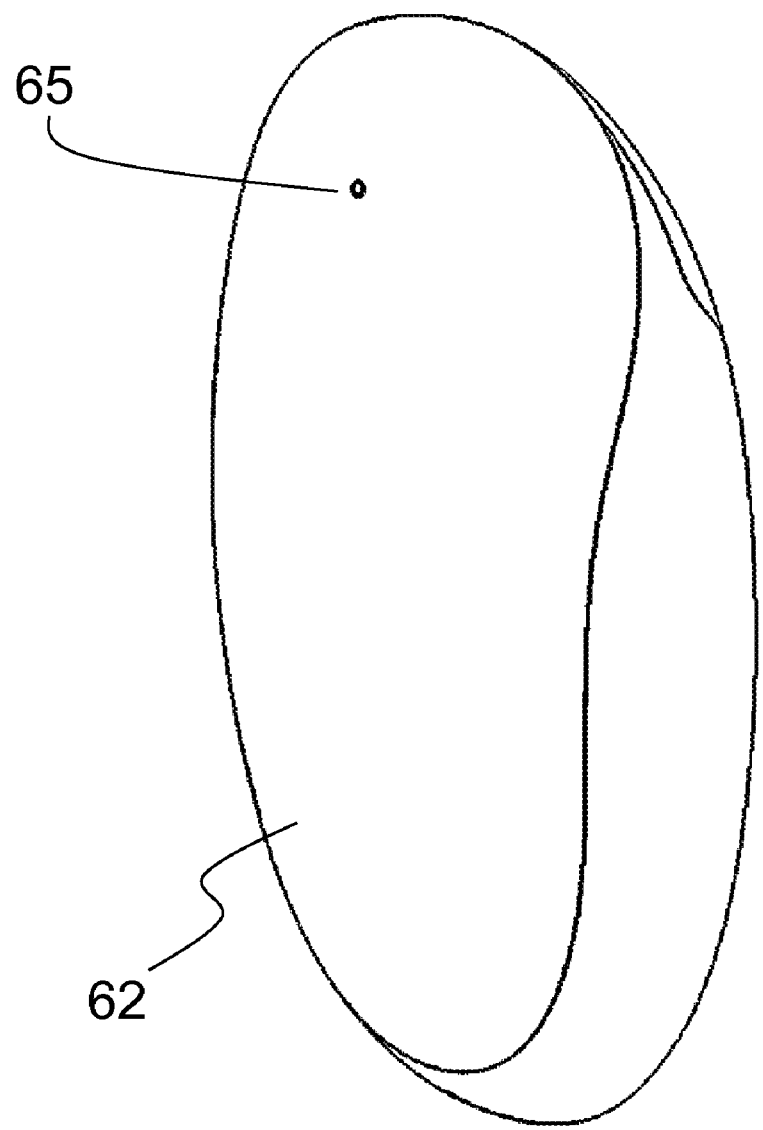
FIG. 6A is a schematic diagram illustrating a typical exterior shape of the device according to the present invention.
Figure 6B:
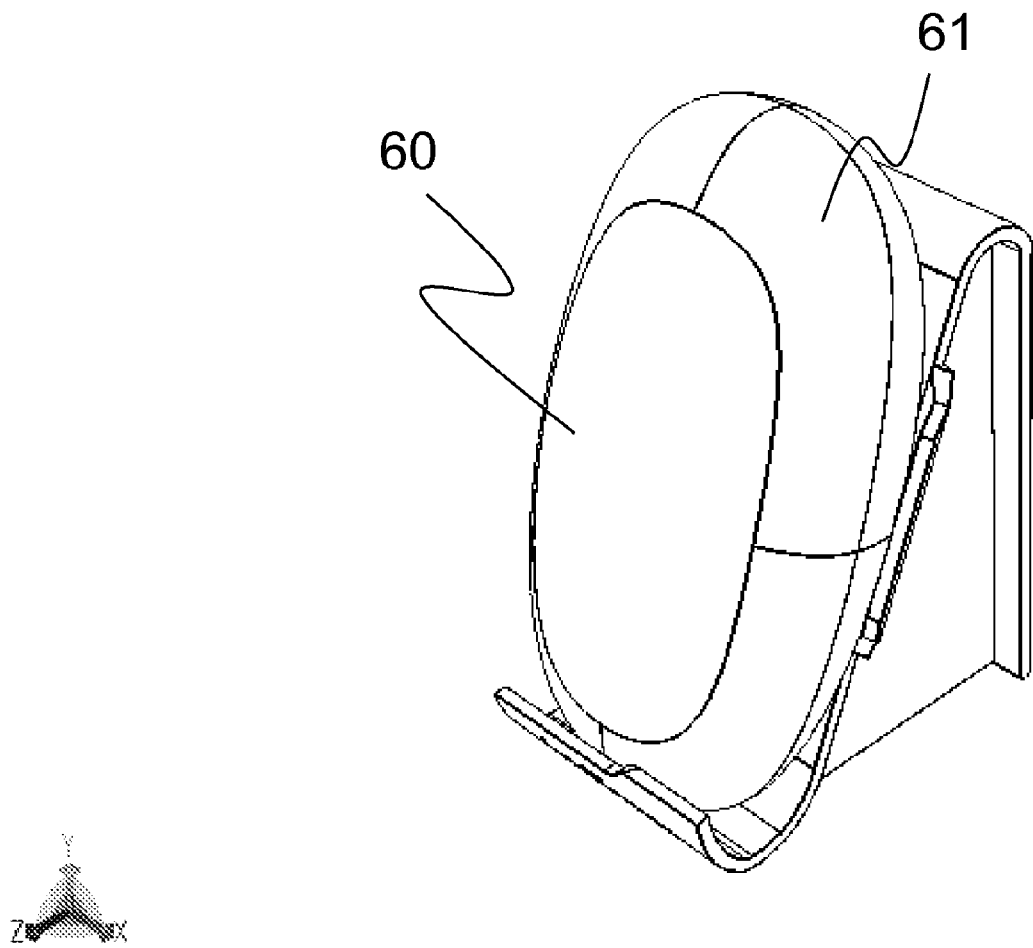
FIG. 6B is a schematic diagram illustrating the perspective view of the device which is placed in a wireless recharger.
Figure 6C:
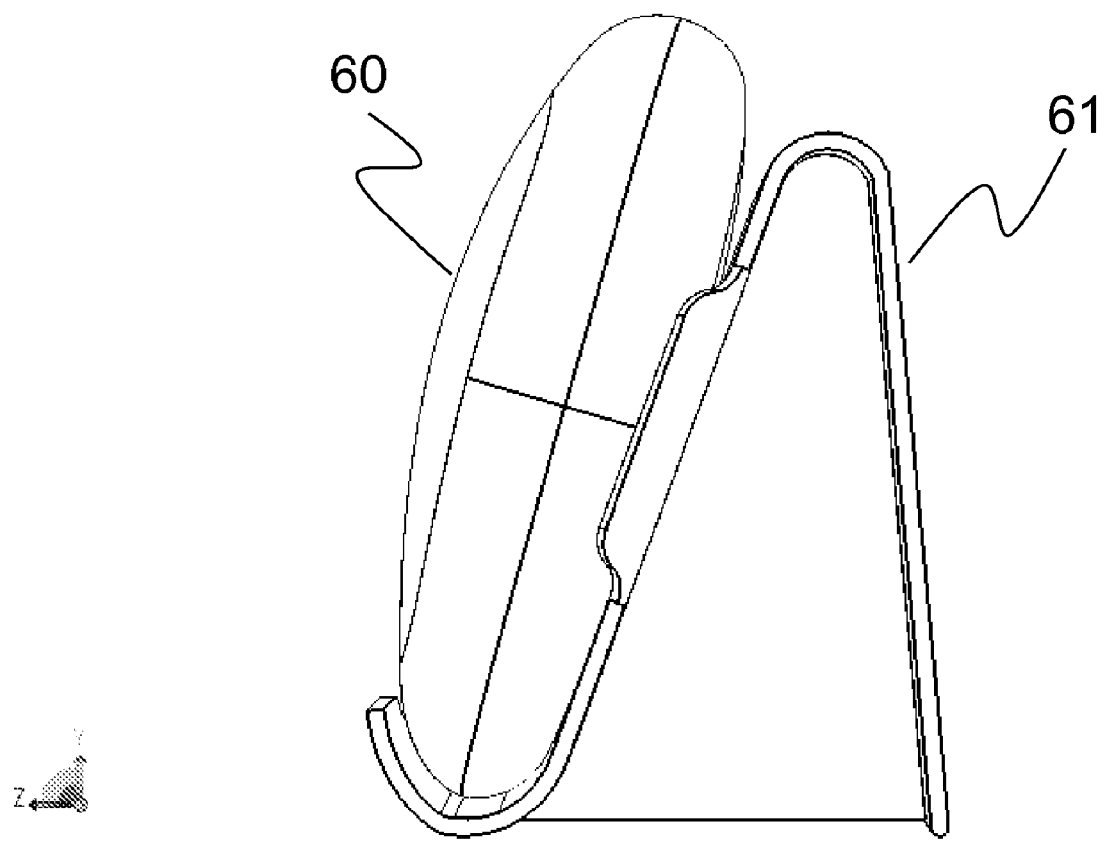
FIG. 6C is a schematic diagram illustrating a side view of the FIG. 6B.

In the most preferred mode, the enclosure body 11 is in an easy-holding oval shape and includes two continuous pieces—front and back pieces—which are mechanically coupled together. The specimen outlet 15 is on the front piece 13 immediately coupled to the ultrasonic transmission plate 12. In use, the back piece is for palm-holding. The device includes a wireless charger and thus it can be charged wirelessly. So, except the specimen outlet 15, the device does not have any other outlet or connectors. As an example, FIG. 6A-FIG. 6C illustrates a typical exterior shape of the device 60 according to the present invention, wherein it contains a skin treatment surface 62 as a front piece and a specimen outlet 65 on the treatment surface 62. The device 60 can be wirelessly charged when it is placed in the recharger frame 61 as shown in FIG. 6B and FIG. 6C.

The dispenser 14 may have any of the below features: (1) the dispenser 14 can be removable as illustrated in FIG. 1D where dispenser 14 is removed from the enclosure body 11 and leaving an emptied space 143, in other words, it may be taken out and installed back into the enclosure body 11 by the user; (2) the specimen 19 may be replenished within dispenser 14 by the user after depletion of the specimen during skin beatification process, i.e. dispenser 14 may be re-used; (3) the dispenser 14 may be disposable and for one-time use only, where specimen 19 is pre-filled within the dispenser before usage; (4) the dispenser 14 can be configured as multiple sub-dispensers 143 containing same or different specimens such that the dispensers can be individually selected to dispense contained specimen; (5) the dispenser 14 can also be configured as a single dispenser with multiple specimen compartments 143 that may contain same or different specimens, such that each compartment within the dispenser can be individually selected and dispense specimen; (6) the dispensing of the specimen 19 is fulfilled by a manually exerted force to the dispenser, upon which a pressure generation component that is part of the dispenser, for example a lead, a lever, a gauge, a cap, a piston, or a stretched porch, forces the specimen 19 to flow out of the dispenser through the outlet 15; (7) the dispensing of the specimen 19 is fulfilled by an electrically powered driving mechanism that is part of the dispenser and operated by the electrical interface 140 located within the enclosure 11 body; (8) the dispensing of the specimen 19 is fulfilled by an electrically powered driving mechanism that is part of the device and electrically controlled by the control unit 17. The driving mechanism forces the specimen 19 to flow out of the dispenser through the outlet 15.

In other words, the dispenser 14 can be any of: a removable and replaceable dispenser; a refillable dispenser; a disposable and for one-time use only dispenser; an integrated dispenser having multiple sub-dispensers 143 containing same or different specimens, the sub-dispensers 143 being individually selected to dispense specimen therein; and an integrated dispenser with multiple specimen compartments 143 containing same or different specimens, each of the compartments 143 being individually selected to dispense specimen therein.

The dispenser 14 may also have any of the following seven (7) features with through one or more electrical contacts 141 that exist on the dispenser 14:

Feature 1: The dispenser 14 may include an embedded specimen dispensing or releasing mechanism 145 that is controlled by the electronic control unit 17 through the electrical interface 140 and the contacts 141.

Feature 2: The dispenser 14 may include an embedded data storage device 142 as shown in FIG. 1C for storing information such as, but not limited to: (1) information of the specimen contained within the dispenser 14, which can be, but not limited to, specimen brand, name, type, original, composition, production date and expiration date, specimen level within the dispenser and ordering information; (2) information of optimal or pre-set operational mode of the ultrasonic generator 16 through the electronic control unit 17 when the specimen 19 contained in dispenser 14 is to be used, where the operational mode can be, but not limited to, timing, ultrasonic vibration strength and location of the operation to be generated on transmission plate 12; (3) information of optimal or pre-set operational mode of the different dispensers 14 or difference specimen compartments within a single dispenser, where the operational mode can be, but not limited to, timing of specimen application from each different dispenser or each different compartment, amount of specimen to be dispensed from each different dispenser or each different compartment; (4) the information of historic usage data of the device, the dispenser and specimen; and (5) information that is created or input by the user; and (6) biographic information of the user.

Feature 3: The electronic control unit 17 may receive data stored in the dispenser 14 to convey information to the user through visual, skin contact or sound effects.

Feature 4: Alternatively, the electronic control unit 17 may receive data stored in the data storage device 142 of the dispenser 14 to operate the ultrasonic generator 16 in a specific manner determined by the information stored in the said data.

Feature 5: The control unit 17 may also comprise another embedded data storage device 172 for storing information such as, but not limited to, device operation data, user skin information data, user personal and biometrics information, dispenser identification data. Such stored information may be updated as needed. Control unit 17 may also contain embedded programs that utilize all the information stored in the data storage device 172 of the control unit 17 and the data storage device 142 of dispenser 14 to operate and control the serum dispensing from dispenser 14, as well as the ultrasound generator 16. Such embedded programs may also be updated for better function.

Feature 6: Alternatively, the electronic control unit 17 may send data to be stored in the data storage device 142 of the dispenser 14.

Feature 7: The dispenser 14 may be recovered by the manufacture and data stored within the data storage device 142 of the dispenser 14 may be retrieved.

Although FIGS. 1A and 1B show dispenser 14 residing within the enclosure body 11, in practice the dispenser 14 may also be externally attached to the enclosure body 11. However, when attached, the lotion 19 is still dispensed through a conduit 151 as shown in FIG. 1B through FIG. 1D that connects from the inside to the outside of the enclosure body 11 and finally through the outlet 15. Thus, the attached dispenser 14 still functions as an integral part of the device.

Second Embodiment

Figure 2A:
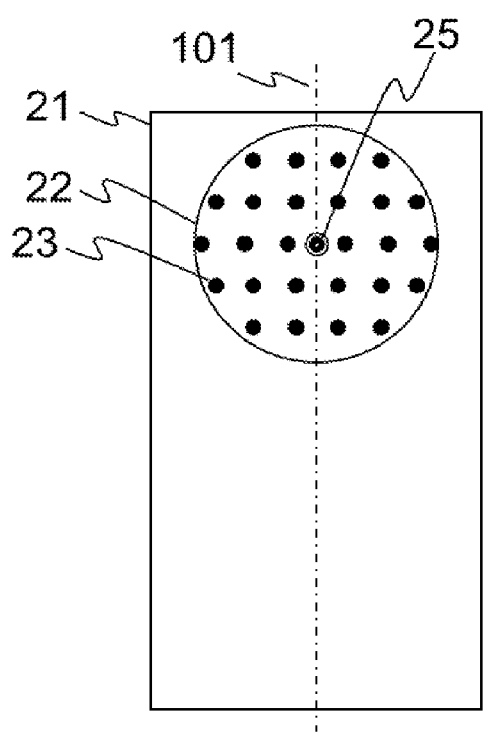
FIG. 2A is a schematic diagram illustrating the front view of the device according to the second preferred embodiment of the present invention.
Figure 2B:
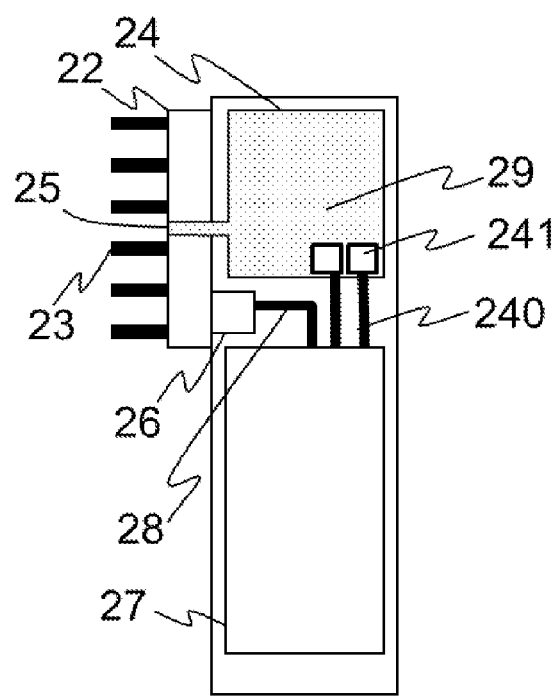
FIG. 2B is a schematic diagram illustrating a cross-sectional view of the device according to the second preferred embodiment of the present invention.

FIG. 2A and FIG. 2B illustrate the second preferred embodiment of the present invention, where a specimen dispenser is integrated within an electrically powered brush device for skin treatment. FIG. 2A shows the front view of the device and FIG. 2B shows the cross-section view along the center line 101 of FIG. 2A.

The device according to this embodiment includes the following components: (1) an enclosure body 21 made of metal, alloy or plastics; (2) a brush head 22, which can have any of rotational, tapping, pulsating and vibration movements during skin treatment that are powered and controlled by a brush head driver 26; (4) various brush fiber 23 for skin treatment being attached to the brush head; (5) a skin treatment specimen container and dispenser 24 that contains a skin treatment specimen 29, which can be, but not limited to, liquid, gel, cream, paste and powder; (6) a specimen outlet 25 that is either in the form of a clearance into the brush head surface where brush fiber(s) 23 are disposed, or in the form of a tube extruding from the brush head surface to a height slightly shorter than the maximum length of the brush fibers, and through the specimen outlet 25, the specimen 29 is dispensed to the surface of the brush head 22 and, preferably, to the brush fibers 23 that are to be in contact with the skin during skin treatment; (7) an electronic control unit 27 containing electrical circuits, electronic components and necessary embedded software exists within the enclosure body 21; (8) an electrical interface 28 that exists between the brush head driver 26 and an electronic control unit 27 so that the performance of the brush head driver 26 can be controlled by the electronic control unit 27, where the electronic control unit 27 controls the motion of the brush head 22 via the brush head driver 26 and may, optionally, also provide user interface, power supply and charging functions. Additionally, the electronic control unit 27 may send electrical signals to the specimen dispenser 24 or receives electrical signals from the specimen dispenser 24 to achieve required skin treatment procedure through another electrical interface 240 that connects to the electrical contacts 241 on dispenser 24.

The dispenser 24 may have any of the below features: (1) the dispenser 24 is removable, i.e., it may be taken out and installed back into the enclosure body 21 by the user; (2) the specimen 29 may be replenished within dispenser 24 by the user after depletion of the specimen during skin beatification process, i.e. dispenser 24 may be re-used; (3) the dispenser 24 may be disposable and for one-time use only, where specimen 29 is pre-filled within the dispenser before usage; (4) the dispenser 24 can be configured as multiple dispensers containing same or different specimens may be installed in one enclosure body 21, such that dispensers can be individually selected to dispense contained specimen; (5) the dispenser 24 can be configured as a single dispenser with multiple specimen compartments that may contain same or different specimens, such that each compartment within the dispenser can be individually selected and dispense specimen; (6) the dispensing of the specimen 29 is fulfilled by a manually exerted force to the dispenser, upon which a pressure generation component that is part of the dispenser, for example a lead, a lever, a gauge, a cap, a piston, or a stretched porch, forces the specimen 29 to flow out of the dispenser through the outlet 25; and (7) the dispensing of the specimen 29 is fulfilled by an electrically powered driving mechanism that is part of the dispenser and operated by the electrical interface 240 located within the enclosure 21 body; (8) the dispensing of the specimen 29 is fulfilled by an electrically powered driving mechanism that is part of the device and electrically controlled by the control unit 27. The driving mechanism forces the specimen 29 to flow out of the dispenser through the outlet 25.

The dispenser 24 may also include an embedded specimen dispensing or releasing mechanism within the dispenser 24 that is controllable by the electronic control unit 27 through the electrical interface 240 and one or more electrical contacts 241 embedded in the dispenser 24.

The dispenser 24 may also include an embedded memory or data storage device 242 within dispenser 24 for storing information such as, but not limited to:

data stored in digital format by an embedded memory or data storage device within dispenser 24 that may contain any of the below information: (1) information of the specimen contained within the dispenser, such as but not limited to, specimen brand, name, type, original, composition, production date and expiration date, specimen level within the dispenser and ordering information; (2) information of optimal or pre-set operational mode of the brush head 22 through the control electronics 27 when the specimen 29 contained in dispenser 24 is to be used, such as but not limited to, timing, motion type, motion strength and sequence of motions of the brush head 22; (3) information of optimal or preset operational mode of the different dispensers 24 or difference specimen compartments within a single dispenser, such as but not limited to, timing of specimen application from each different dispenser or each different compartment, amount of specimen to be dispensed from each different dispenser or each different compartment; (4) information of historic usage data of the device, the dispenser and specimen; (5) information that is created or input by the user; and (6) biographic information of the user.

The electronic control unit 27 may receive data stored in the dispenser 24 to display information to the user through visual, skin contact or sound effects.

The electronic control unit 27 may receive data stored in the dispenser 24 to operate the brush head 22 in a specific manner determined by the information stored in the said data;

The control unit 27 may also comprise another embedded memory or data storage device for storing information such as, but not limited to, device operation data, user skin information data, user personal and biometrics information, dispenser identification data. Such stored information may be updated as needed. Control unit 27 may also contain embedded programs that utilize all the information stored in the control unit 27 and dispenser 24 to operate and control the serum dispensing from dispenser 24, as well as the brush head driver 26. Such embedded programs may also be updated for better function.

Alternatively, the electronic control unit 27 may send data to be stored in the dispenser 24.

The dispenser 24 may be recovered by the manufacture and data stored within dispenser 24 may be retrieved.

Although FIGS. 2A and 2B show dispenser 24 residing within the enclosure body 21, in practice the dispenser 24 may also be externally attached to the enclosure body 21. However, when attached, the lotion 29 is still dispensed through a conduit that connects from the inside to the outside of the enclosure body 21 and finally through the outlet 25. Thus, the attached dispenser 24 still functions as an integral part of the device.

Third Embodiment

Figure 3A:
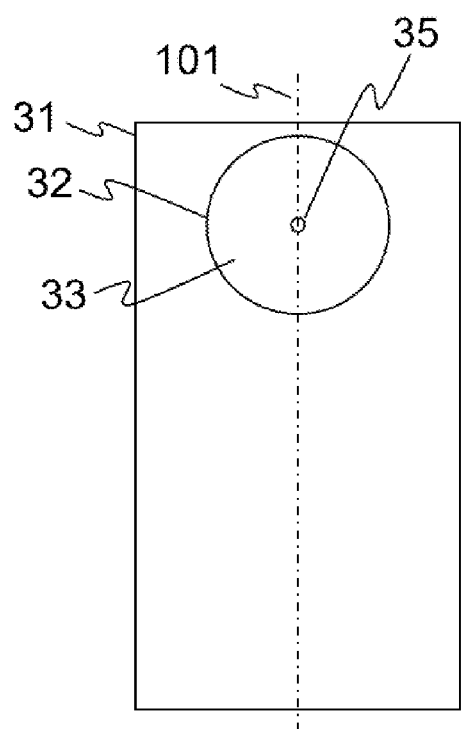
FIG. 3A is a schematic diagram illustrating the front view of the device according to the third preferred embodiment of the present invention.
Figure 3B:
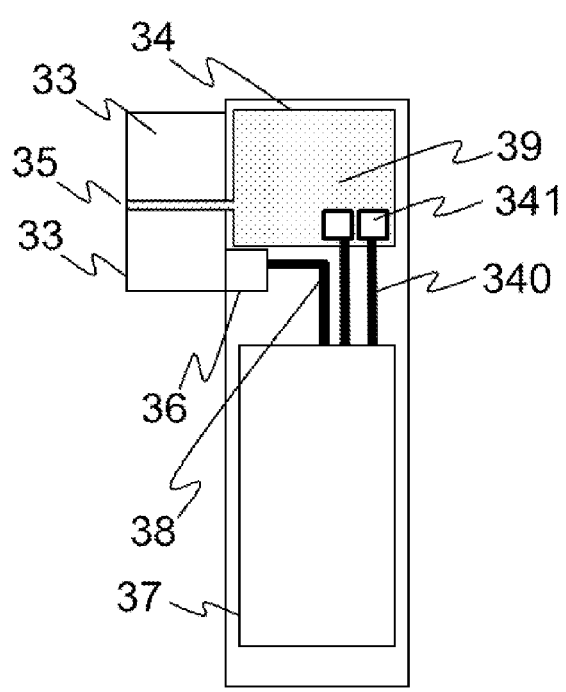
FIG. 3B is a schematic diagram illustrating a cross-sectional view of the device according to the third preferred embodiment of the present invention.

FIG. 3A and FIG. 3B illustrates the third preferred embodiment of the current invention, where a specimen dispenser is integrated within an electrically powered skin massaging device for skin treatment. FIG. 3A shows the front view of the proposed device. FIG. 3B shows the cross-section view along the center line 101 of FIG. 3A.

The embodiment contains the following components: (1) an enclosure body 31 made of metal, alloy or plastics or a combination thereof; (2) a skin massaging tip 32 for contacting the skin with a treatment surface 33 and transmitting the mechanical massaging motion to the target skin area, where the massaging motion of the massaging tip can be, but not limited to, vibration, pulsating, rotation, tapping, expansion and contraction; (3) a motion generator 36 which generates the massaging motions; (4) a skin treatment specimen container and dispenser, herein after collectively referred to as dispenser 34, that contains specimen 39 which can be, but not limited to, liquid, gel, cream, paste and powder; (5) an specimen outlet 35 existing on the same continuous surface 33 of the massaging tip 32, through which skin treatment specimen 39 is dispensed close to or preferably, directly on top of the massaging tip 32 surface 33 that is to be in contact with the skin during skin treatment; (6) an electronic control unit 37 containing electrical circuits, electronic components and necessary embedded software exists within the enclosure body 31; and (7) an electrical interface 38 located between the motion generator 36 and the electronic control unit 37 so that the performance of the massaging tip 32 can be controlled by the electronic control unit.

The electronic control unit 37 controls the motions of the massaging tip 32 and it may, alternatively, also provide user interface, power supply and charging functions. Additionally, the electronic control unit 37 may send electrical signals to the specimen dispenser 34 or receives electrical signals from the specimen dispenser 34 to achieve the required skin treatment procedure through another electrical interface 340 that connects to the electrical contacts 341 on dispenser 34.

The dispenser 34 may have any of the below features: (1) the dispenser 34 may be taken out and installed back into the enclosure body 31 by the user; (2) the specimen 39 may be replenished within the dispenser 34 by the user after depletion of the specimen during skin beatification process, i.e. dispenser 34 may be re-used; (3) the dispenser 34 may be disposable and for one-time use only, where the specimen 39 is pre-filled within the dispenser before usage; (4) the dispenser 34 can be configured as multiple dispensers containing same or different specimens may be installed in a single enclosure body 31, such that dispensers can be individually selected to dispense contained specimen; (5) the dispenser 34 can be configured as a single dispenser with multiple specimen compartments that may contain same or different specimens, such that each compartment within the dispenser can be individually selected and dispense specimen; (6) the dispensing of the specimen 39 is fulfilled by a manually exerted force to the dispenser, upon which a pressure generation component that is part of the dispenser, for example a lead, a lever, a gauge, a cap, a piston, or a stretched porch, forces the specimen 39 to flow out of the dispenser through the outlet 35; (7) the dispensing of the specimen 39 is fulfilled by an electrically powered driving mechanism that is part of the dispenser and operated by the electrical interface 340 located within the enclosure 31 body; (8) the dispensing of the specimen 39 is fulfilled by an electrically powered driving mechanism that is part of the device and electrically controlled by the control unit 37. The driving mechanism forces the specimen 39 to flow out of the dispenser through the outlet 35.

The dispenser 34 may also include a specimen dispensing or releasing mechanism embedded in the dispenser 34. The embedded specimen dispensing or releasing mechanism is controlled by the electronic control unit 37 through the electrical interface 340 and various electrical contacts 341 embedded in the dispenser 34.

The dispenser 34 may also include an embedded memory or data storage device for storing information, such as but limited to: (1) the information of the specimen contained within the dispenser, such as but not limited to, specimen brand, name, type, original, composition, production date and expiration date, specimen level within the dispenser and ordering information; (2) information of optimal or pre-set operational mode of the massaging tip 32 through the electronic control unit 37 when the specimen 39 contained in dispenser 34 is to be used, such as but not limited to, timing, motion type, motion strength and the sequence of motions of the massaging tip 32; (3) the information of optimal or pre-set operational mode of the different dispensers 34 or difference specimen compartments within a single dispenser, such as but not limited to, timing of specimen application from each different dispenser or each different compartment, amount of specimen to be dispensed from each different dispenser or each different compartment; (4) the information of historic usage data of the device, the dispenser and specimen; (5) the information that is created or input by the user; and (6) the biographic information of the user.

The electronic control unit 37 may receive data stored in the dispenser 34 to display information to the user through visual, skin contact or sound effects.

The electronic control unit 37 may, alternatively, also receive data stored in the dispenser 34 to operate the massaging tip 32 in a specific manner determined by the information stored in the said data.

The control unit 37 may also comprise another embedded memory or data storage device for storing information such as, but not limited to, device operation data, user skin information data, user personal and biometrics information, dispenser identification data. Such stored information may be updated as needed. Control unit 37 may also contain embedded programs that utilize all the information stored in the control unit 37 and dispenser 34 to operate and control the serum dispensing from dispenser 34, as well as the motion generator 36. Such embedded programs may also be updated for better function.

The electronic control unit 37 may send data to be stored in the dispenser 34.

The dispenser 34 may be recovered by the manufacture and data stored within the dispenser 34 may be retrieved.

Although FIGS. 3A and 3B show dispenser 34 residing within the enclosure body 31, in practice the dispenser 34 may also be externally attached to the enclosure body 31. However, when attached, the lotion 39 is still dispensed through a conduit that connects from the inside to the outside of the enclosure body 31 and finally through the outlet 35. Thus, the attached dispenser 34 still functions as an integral part of the device.

Fourth Embodiment

Figure 4A:
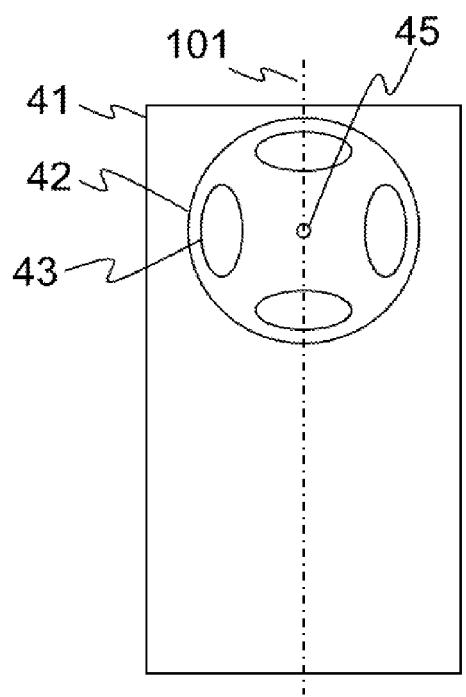
FIG. 4A is a schematic diagram illustrating the front view of the device according to the fourth preferred embodiment of the present invention.
Figure 4B:
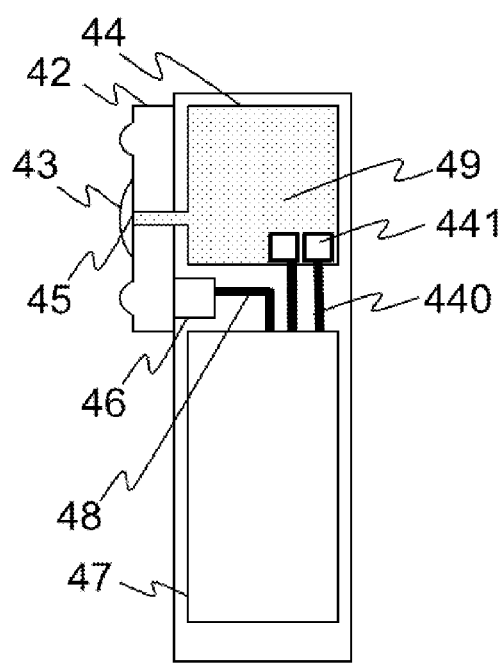
FIG. 4B is a schematic diagram illustrating a cross-sectional view of the device according to the fourth preferred embodiment of the present invention.

FIG. 4A and FIG. 4B illustrate the fourth preferred embodiment of the current invention, where a specimen dispenser is integrated within an electrically powered galvanic skin treatment device that produces electric current flowing along skin surface and/or through skin cells. FIG. 4A shows the front view of the proposed device. FIG. 4B shows the cross-section view along the center line 101 of FIG. 4A.

The embodiment contains the following components: (1) an enclosure body 41 made of metal, alloy or plastics or a combination thereof; (2) a galvanic skin treatment head 42 for contacting the skin with one or more electrodes 43 and producing electric voltage and current on the target skin area; (3) a voltage or current driver 46 which generates the electric voltage or current; (4) a skin treatment specimen container and dispenser, collectively referred to as dispenser 44 that contains specimen 49 that can be, but not limited to, liquid, gel, cream, paste and powder; (5) a specimen outlet 45 existing on the surface of the treatment head 42 where the electrodes 43 reside, through the specimen outlet 45, the skin treatment specimen 49 is dispensed close to or, preferably, directly on top of one or more of the electrodes 43 that are to be in contact with the skin during skin treatment; (6) an electronic control unit 47 containing electrical circuits, electronic components and necessary embedded software exists within the enclosure body 41; and (7) an electrical interface 48 located between the voltage or current driver 46 and the electronic control unit 47 so that the voltage or current exerted by the electrodes 43 on the skin can be controlled by the electronic control unit.

The electronic control unit 47 controls the electrode 43 by the voltage or current driver 46, and may also provide user interface, power supply and charging functions. Additionally, the electronic control unit 47 may send electrical signals to the specimen dispenser 44 or receives electrical signals from the specimen dispenser 44 to achieve required skin treatment procedure through another electrical interface 440 that connects to the electrical contacts 441 on dispenser 44.

The dispenser 44 may have any of the below features: (1) the dispenser 44 is removable, i.e., may be taken out and installed back into the enclosure body 41 by the user; (2) the specimen 49 may be replenished within dispenser 44 by the user after depletion of the specimen during skin beatification process, i.e. dispenser 44 may be re-used; (3) the dispenser 44 may be disposable and for one-time use only, where the specimen 49 is pre-filled within the dispenser before usage; (4) the dispenser 44 may be configured as multiple dispensers 44 containing same or different specimens, such that dispensers can be individually selected to dispense contained specimen; (5) the dispenser 44 may be configured as a single dispenser with multiple specimen compartments that may contain same or different specimens, such that each compartment within the dispenser can be individually selected and dispense specimen; (6) the dispensing of the specimen 49 is fulfilled by a manually exerted force to the dispenser, upon which a pressure generation component that is part of the dispenser, for example a lead, a lever, a gauge, a cap, a piston, or a stretched porch, forces the specimen 49 to flow out of the dispenser through the outlet 45; (7) the dispensing of the specimen 49 is fulfilled by an electrically powered driving mechanism that is part of the dispenser and operated by the electrical interface 440 located within the enclosure 41 body; (8) the dispensing of the specimen 49 is fulfilled by an electrically powered driving mechanism that is part of the device and electrically controlled by the control unit 47. The driving mechanism forces the specimen 49 to flow out of the dispenser through the outlet 45.

The dispenser 44 may also include an embedded specimen dispensing or releasing mechanism within the dispenser 44. The embedded specimen dispensing or releasing mechanism is controlled by the electronic control unit 47 through the electrical interface 440 and various electrical contacts 441 embedded in the dispenser 44.

The dispenser 44 may also include an embedded memory or data storage device for storing information, such as but not limited to: (1) the information of the specimen contained within the dispenser, such as but not limited to specimen brand, name, type, original, composition, production date and expiration date, specimen level within the dispenser and ordering information; (2) the information of optimal or pre-set operational mode of electrodes 43 through the control electronics 47 when the specimen 49 contained in dispenser 44 is to be used, such as but not limited to, timing, voltage or current type (DC or AC), voltage or current level, voltage or current temporal waveform, and frequency of the voltage or current applied by the electrodes 43 to the skin; (3) the information of optimal or pre-set operational mode of the different dispensers 44 or difference specimen compartments within a single dispenser, such as but not limited to, timing of specimen application from each different dispenser or each different compartment, amount of specimen to be dispensed from each different dispenser or each different compartment; (4) the information of historic usage data of the device, the dispenser and specimen; (5) the information that is created or input by the user; and (6) the biographic information of the user.

The electronic control unit 47 may receive data stored in the dispenser 44 to display information to the user through visual, skin contact or sound effects.

The electronic control unit 47 may receive data stored in the dispenser 44 to operate the electrodes 43 in a specific manner determined by the information stored in the said data.

The control unit 47 may also comprise another embedded memory or data storage device for storing information such as, but not limited to, device operation data, user skin information data, user personal and biometrics information, dispenser identification data. Such stored information may be updated as needed. Control unit 47 may also contain embedded programs that utilize all the information stored in the control unit 47 and dispenser 44 to operate and control the serum dispensing from dispenser 44, as well as the voltage or current driver 46. Such embedded programs may also be updated for better function.

The electronic control unit 47 may send data to be stored in the dispenser 44

The dispenser 44 may be recovered by the manufacture and data stored within dispenser 44 may be retrieved.

Although FIGS. 4A and 4B show dispenser 44 residing within the enclosure body 41, in practice the dispenser 44 may also be externally attached to the enclosure body 41. However, when attached, the lotion 49 is still dispensed through a conduit that connects from the inside to the outside of the enclosure body 41 and finally through the outlet 45. Thus, the attached dispenser 44 still functions as an integral part of the device.

Fifth Embodiment

Figure 5A:
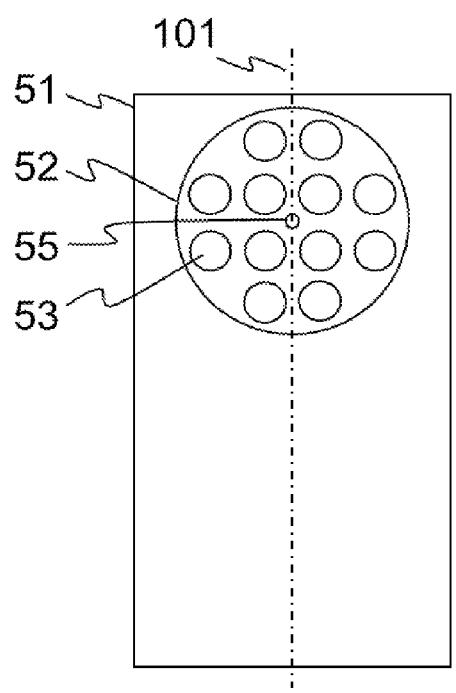
FIG. 5A is a schematic diagram illustrating the front view of the device according to the fifth preferred embodiment of the present invention.
Figure 5B:
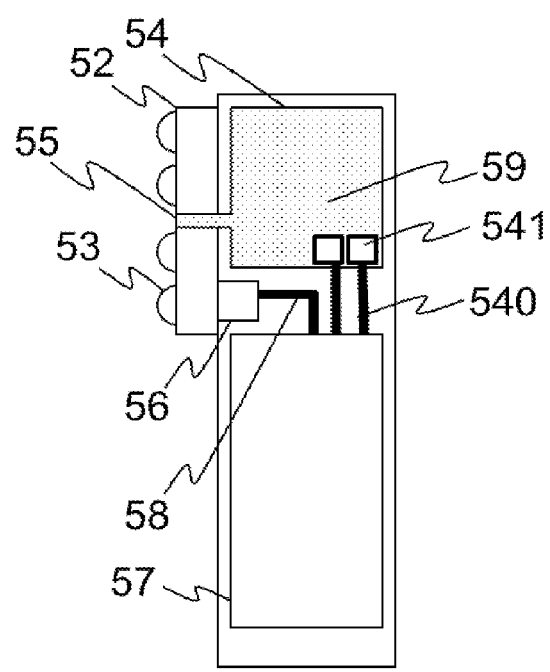
FIG. 5B is a schematic diagram illustrating a cross sectional view of the device according to the fifth preferred embodiment of the present invention.

FIG. 5A and FIG. 5B illustrates the fifth preferred embodiment of the current invention, where a specimen dispenser is integrated within an electrically powered light illumination device for skin treatment. FIG. 5A shows the front view of the proposed device. FIG. 5B shows the cross-section view along the center line 101 of FIG. 5A.

The embodiment contains the following components: (1) an enclosure body 51 made of metal, alloy or plastics or a combination thereof; (2) a lightening housing 52 for treating skin with light illumination generated by one or more lightening units 53 which are powered by a light controller 56; (3) a skin treatment specimen container and dispenser, collectively referred to as dispenser 54 that contains specimen 59 which can be, but not limited to, liquid, gel, cream, paste and powder; (4) a specimen outlet 55 existing on the surface of the lighting housing 52 where lightening units 53 reside, through the outlet 55, the skin treatment specimen 59 is dispensed either on the surface of the housing unit, or directly onto the skin area to be treated; (5) an electronic control unit 57 containing electrical circuits, electronic components and necessary embedded software exists within the enclosure body 51; and (6) an electrical interface 58 located between the light controller 56 and the electronic control unit 57 so that the light emission from the lightening unit 53 can be controlled by the electronic control unit 57.

The electronic control unit 57 controls the lightening unit 53 via the lightening controller 56. It may also provide user interface, power supply and charging functions. Additionally, the electronic control unit 57 may send electrical signals to the specimen dispenser 54 or receives electrical signals from the specimen dispenser 54 to achieve required skin treatment procedure through another electrical interface 540 that connects to the electrical contacts 541 on dispenser 54.

The dispenser 54 may have any of the below features: (1) the dispenser 54 is removable, i.e., it may be taken out and installed back into the enclosure body 51 by the user; (2) the specimen 59 may be replenished within dispenser 54 by the user after depletion of the specimen during skin beatification process, i.e. dispenser 54 may be re-used; (3) the dispenser 54 may be disposable and for one-time use only, where specimen 59 is pre-filled within the dispenser before usage; (4) the dispenser 54 may be configured as multiple dispensers containing same or different specimens, such that the dispensers can be individually selected to dispense contained specimen; (5) the dispenser 54 may be configured as a single dispenser with multiple specimen compartments that may contain same or different specimens, such that each compartment within the dispenser can be individually selected and dispense specimen; (6) the dispensing of the specimen 59 is fulfilled by a manually exerted force to the dispenser, upon which a pressure generation component that is part of the dispenser, for example a lead, a lever, a gauge, a cap, a piston, or a stretched porch, forces the specimen 59 to flow out of the dispenser through the outlet 55; (7) the dispensing of the specimen 59 is fulfilled by an electrically powered driving mechanism that is part of the dispenser and operated by the electrical interface 540 located within the enclosure 51 body; (8) the dispensing of the specimen 59 is fulfilled by an electrically powered driving mechanism that is part of the device and electrically controlled by the control unit 57, where the driving mechanism forces the specimen 59 to flow out of the dispenser through the outlet 55.

The dispenser 54 may also include a specimen dispensing or releasing mechanism which is controlled by the electronic control unit 57 through the electrical interface 540 and various electrical contacts 541 embedded in the dispenser 54.

The dispenser 54 may also include a memory or data storage device embedded in the dispenser 54 that may store information, such as but not limited to: (1) the information of the specimen contained within the dispenser such as but not limited to, specimen brand, name, type, original, composition, production date and expiration date, specimen level within the dispenser and ordering information; (2) the information of optimal or pre-set operational mode of lightening unit 53 through the control electronics 57 when the specimen 59 contained in dispenser 54 is to be used, such as but not limited to, timing, light power, light duration, light wavelength and sequence of different lightening schemes that are emitted by the lightening unit 53; (3) the information of optimal or pre-set operational mode of the different dispensers 54 or difference specimen compartments within a single dispenser, such as but not limited to, timing of specimen application from each different dispenser or each different compartment, amount of specimen to be dispensed from each different dispenser or each different compartment; (4) the information of historic usage data of the device, the dispenser and specimen; (5) the information that is created or input by the user; (6) the biographic information of the user.

The electronic control 57 may receive data stored in the dispenser 54 to display information to the user through visual, skin contact or sound effects.

The electronic control 57 may also receive data stored in the dispenser 54 to operate the lightening units 53 in a specific manner determined by the information stored in the said data.

The electronic control 57 may also send data to be stored in the dispenser 54.

The control unit 57 may also comprise another embedded memory or data storage device for storing information such as, but not limited to, device operation data, user skin information data; user personal and biometrics information, dispenser identification data. Such, stored information may be updated as needed. Control unit 57 may also contain embedded programs that utilize all the information stored in the control unit 57 and dispenser 54 to operate and control the serum dispensing from dispenser 54, as well as the light controller 56. Such embedded programs may also be updated for better function.

The electronic control 57 may send data to be stored in the dispenser 54

The dispenser 54 may be recovered by the manufacture and the data stored within dispenser 54 may be retrieved.

Although FIGS. 5A and 5B show dispenser 54 residing within the enclosure body 51, in practice the dispenser 54 may also be externally attached to the enclosure body 51. However, when attached, the lotion 59 is still dispensed through a conduit that connects from the inside to the outside of the enclosure body 51 and finally through the outlet 55. Thus, the attached dispenser 54 still functions as an integral part of the device.

The present invention has numerous advantages over the prior arts. For examples: (1) the integrated specimen dispenser with various electronic skin treatment devices enhances the portability and flexibility of the skin treatment process; (2) the integrated specimen dispenser with electrical interface, together with the embedded memory within the dispenser or the control unit, enables customizability of the various electronic devices to provide treatment methods that are specific for each individual's own skin care need, including personalized skin care product synthesized at the spot of treatment; and (3) with the integrated dispenser containing product information, best mode of operation, pre-set beautification process and usage data, the device greatly increases the positive effect of the skin beautification process, reduces the complexity of the user's operation and provides means of feedback from user to manufacture for further improvement on the skin care products.

While one or more embodiments of the present invention have been illustrated above, the skilled artisan will appreciate that modifications and adoptions to those embodiments may be made without departing from the scope and spirit of the present invention.

The invention claimed is:

1. A device used for skin treatment by applying a series of ultrasound vibrations and by dispensing specimen to a target skin area, comprising:
   a skin treatment member for treating the target skin area with ultrasound vibrations which are generated by an ultrasound generator; and
   a specimen outlet embedded in said skin treatment member, said outlet being coupled to a dispenser containing specimen;
   wherein said dispenser is electrically connected to an electronic control unit through an electrical interface and one or more electrical contacts;
   wherein said control unit controls said skin treatment member's ultrasound vibrations and dispenses of specimen from said dispenser; and
   wherein said dispenser comprises an embedded data storage device, wherein said dispenser comprises multiple sub-dispensers with each sub dispenser containing a different specimen; wherein said embedded data storage device stores information of timing and amount of specimen to be dispensed from each of said multiple sub-dispensers; and wherein said embedded data storage device stores information of ultrasonic vibration strength and location of the ultrasound vibration to be generated on said skin treatment member.

2. The device of claim 1, wherein said specimen is any of liquid, gel, serum, cream, lotion, paste and powder.

3. The device of claim 1, wherein said dispenser is removable.

4. The device of claim 1, wherein said control unit is capable of receiving information stored in said data storage device embedded in said dispenser through said electrical interface and one or more of said electrical contacts.

5. The device of claim 1, wherein said control unit comprises an embedded data storage device to store information including any of: device operation data, user skin information data, user personal and biometrics information, and dispenser identification data.

6. The device of claim 5, wherein said control unit contains programs that utilize the information stored in said data storage device embedded in said control unit and the information stored in said data storage device embedded in said dispenser to control the dispensing of said specimen from said dispenser.

7. The device of claim 5, wherein said control unit contains programs that utilize the information stored in said data storage device embedded in said control unit and the information stored in said data storage device embedded in said dispenser to control said ultrasound generator.

8. The device of claim 4, wherein said control unit operates said skin treatment member in a specific manner determined by data received from said data storage device embedded in the dispenser.

9. The device of claim 1, wherein said control unit sends data to be stored in said data storage device embedded in said dispenser through said electrical interface and one or more of said electrical contacts.

\* \* \* \* \*